United States Patent [19]

Poe

[11] 4,455,688

[45] Jun. 26, 1984

[54] WELDER'S GOGGLES

[76] Inventor: Boyd L. Poe, 3735 Hermes La., Cincinnati, Ohio 45239

[21] Appl. No.: 290,365

[22] Filed: Aug. 5, 1981

[51] Int. Cl.³ ............................................ A61F 9/02
[52] U.S. Cl. ............................................ 2/431; 2/439; 2/441; 2/430; 2/8
[58] Field of Search ............... 2/427, 430, 431, 432, 2/439, 440, 441, 447, 444, 8, 9

[56] References Cited

U.S. PATENT DOCUMENTS

| | | | |
|---|---|---|---|
| 2,598,265 | 5/1952 | Jones | 2/427 |
| 3,267,488 | 8/1966 | Colvin | 2/440 |
| 3,944,345 | 3/1976 | Decorato | 2/447 X |
| 4,114,198 | 9/1978 | Sands | 2/8 |

Primary Examiner—Peter P. Nerbun
Attorney, Agent, or Firm—Wood, Herron & Evans

[57] ABSTRACT

Welder's protective goggles particularly adapted for operators who must use corrective bifocal lenses in their work. The goggles comprise a generally tubular shaped member, having an open end contoured to fit snugly against the face about the eyes of the wearer. The axis of the open end of the tubular member is on approximately the same horizontal plane as the axes of the eyes of the wearer when looking straight ahead. The tubular member also has a closed viewing end which has at least one viewing aperture adapted to receive a safety lens. The axis of the closed viewing end intersects the axis of the open end at an angle from below it. The degree of the included angle formed by the intersecting axes is predetermined so that the tilt thus given to the closed viewing end in relation to the open end is such that the wearer of the goggles when using corrective bifocal lenses underneath them will have an unobstructed view when looking through either corrective section of the bifocal lenses. The tubular member is also provided with means for securing the goggles to the head of the wearer.

2 Claims, 4 Drawing Figures

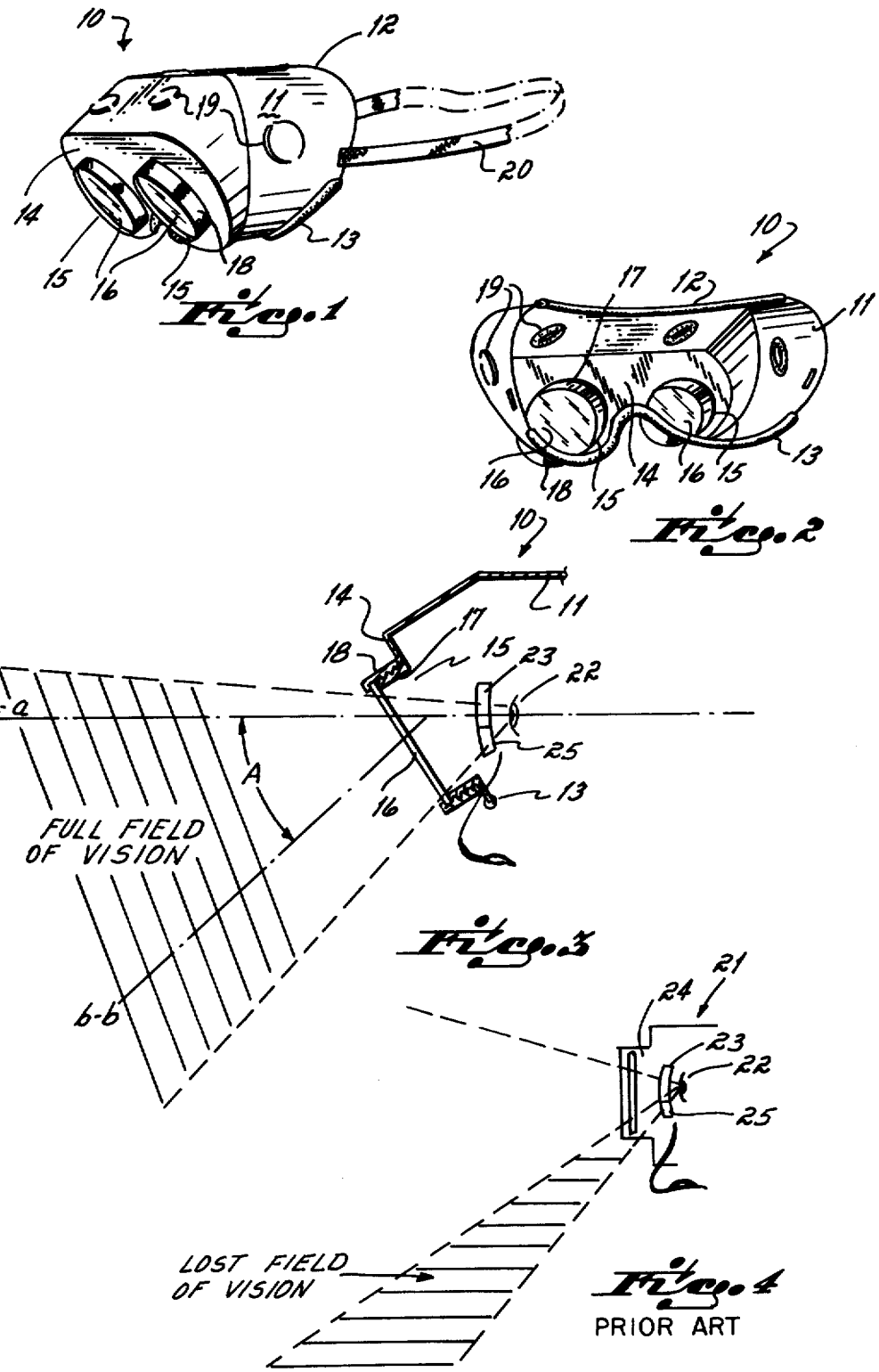

WELDER'S GOGGLES

BACKGROUND OF THE INVENTION

1. Field of the Invention

The present invention relates to eye protective devices. More particularly, the present invention relates to protective goggles for welders and chippers. Still more particularly, the present invention relates to protective goggles for welders and chippers that are especially adapted for operators who must use corrective bifocal lenses in performing their work.

2. Description of the Prior Art

There are available many types of welders and chippers protective goggles of the cup type as well as the single plate type that provide eye protection by fitting snugly against the face surrounding the eyes of the wearer. These, of course, all generally serve well their intended purpose of protecting the eyes of the wearer from injury. None, however, is especially adapted for use by the wearer of corrective glasses, particularly operators for whom it is imperative to wear corrective bifocal lenses when working. Such protective goggles as are available either simply are not designed to accept corrective glasses under them, or, if it is possible to wear glasses under them, the lower rim of the goggle creates an obstruction that is entirely unacceptable particularly for wearers whose glasses have bifocal lenses. It has been left for the operator, then, to try to adapt himself to use such protective goggles as are available through uncomfortable and mostly ineffective head and eye adjustments.

There has been some efforts made to modify existing helmet or shield type protective devices to eliminate or minimize this type of deficiency. Generally, these attempts have simply consisted in providing a longer viewing aperture to the face shield which permits the wearer to use the lower part of his bifocal lenses in viewing his work. One such modified helmet is disclosed in U.S. Pat. No. 4,114,198, the principal feature of which appears to be the provision of a viewing aperture whose contour is designed to minimize the condensation of moisture on the lower part of the aperture lens, i.e., that portion of the lens specifically provided to assist the bifocal lens wearer. While such modifications may be of some use as they relate to protective helmets and face shields, they are not applicable to protective goggles to which the present invention relates.

SUMMARY OF THE INVENTION

It is the principal object of this invention, therefore, to provide protective goggles for welders, chippers, and the like, which are so designed that a user may comfortably and effectively wear corrective glasses under them. It is a further object of this invention to provide such protective goggles that can be worn over corrective bifocal lenses without impairing the vision of the wearer when using either section of the corrective bifocal. It is still a further object of this invention to provide protective goggles of the type referred to that give maximum eye protection and vision with a minimum of wearing discomfort.

Protective goggles intended for use with corrective glasses according to the objects of this invention comprise an eye protective device of the cup or single plate type provided with a tilt lens which gives the wearer unobstructed vision throughout the entire normal field of vision of his corrective glasses. The goggles comprise a generally tubular shaped protective member having an open end contoured so that it fits snugly against the face around the eyes of the wearer. The tubular member is also provided with a closed viewing end provided with at least one viewing aperture adapted to receive a safety lens. The axis of the open end is approximately on the same horizontal plane as the axes of the eyes of the wearer when looking straight ahead. The axis of the closed viewing end intersects the axis of the open end at an angle from below it. The degree of the included angle formed by the intersecting axes is predetermined so as to give a tilt to the closed viewing end in relation to the open end that will permit the wearer of the goggles when using corrective bifocal lenses underneath them to have unobstructed vision through the viewing aperture when looking through either section of the bifocal lenses.

BRIEF DESCRIPTION OF THE INVENTION

FIG. 1 is a perspective view of the protective goggles of this invention.

FIG. 2 is a view of the inside of the protective goggles.

FIG. 3 is a side elevation sketch of the protective goggles showing the lines of sight and the field of vision for a wearer of corrective bifocal lenses.

FIG. 4 is a side elevation sketch similar to FIG. 3 of a conventional pair of protective goggles showing the lines of sight and the field of vision for a wearer of corrective bifocal lenses.

DESCRIPTION OF THE PREFERRED EMBODIMENT

Referring to the drawing, FIG. 1 shows the protective goggles of this invention generally indicated at 10 comprising a generally tubular shaped protective member or housing 11 having an open end 12 contoured at 13, as shown in FIG. 2, so as to fit snugly against the face surrounding the eyes of the wearer. As shown by solid line a—a in FIG. 3, the axis of open end 12 is essentially horizontal and on approximately the same plane as the axes of the eyes of the wearer when looking straight ahead. At the opposite end of tubular member or housing 11 is a closed viewing end 14 provided with two cup type viewing apertures 15 adapted to receive safety lenses 16. Each viewing aperture 15 is surrounded by a threaded boss 17, the exposed or forward end of which is adapted to receive a lens which is held in place by a complementing annular threaded retainer 18, all as conventionally practiced in the art to facilitate the exchange of lenses as, for example, a chipper's clear hardened safety lens for a welder's filter lens.

To this point, the description of the protective goggles has been essentially that of a pair of conventional protective goggles, over which the protective goggles of this invention are an improvement as will be described with reference particularly to FIG. 3. As shown therein, the axis b—b of closed viewing end 14 of tubular member 11 is not coaxial with axis a—a of open end 12 but instead, axis b—b intersects axis a—a at an angle from below the latter. The degree of the included angle A thus formed by the intersecting axes a—a and b—b is such as to provide the necessary tilt to closed viewing end 14 with respect to open end 12 so that a wearer using corrective bifocal lenses underneath the protective goggles will have a full range of vision through both segments of the bifocal lenses, there being no impairment or obstruction created by any part of the protective goggles. Included angle A will preferably be greater than angle 30° but less than 45° in order to impart to closed viewing end 14 the desired tilt necessary to insure the wearer of a full range of unobstructed vision through viewing end 14.

Tubular member or housing 11 is provided with capped air vents 19 to minimize condensation and fogging, and with an adjustable means 20 for securing the protective goggles to the wearer's head. Tubular member 11 may be made of lightweight metal but, preferably, is constructed of any of various suitable commercially available plastic materials. Whatever material is used for constructing member 11, the edges of open end 12 are suitably padded and cushioned for maximum comfort when worn. As a modification of the cup type viewing apertures 15 shown in the drawing, a single viewing aperture, not shown, provided with a single plate lens can be employed. The single viewing aperture can be provided for interchanging lenses as conventionally done in the art with this type of viewing aperture. In this modification, of course, the tilt relationship of viewing end 14 to open 12 is maintained to provide the full range of vision for corrective bifocal lens wearers, which is the feature of this invention.

Referring to FIG. 4, there is shown therein a conventional pair of protective goggles 21 with a wearer's eye and a corrective bifocal lens represented at 22 and 23, respectively. From FIG. 4 it can be seen by the broken vision lines that the corrective lens wearer's vision through viewing aperture 24 is seriously impaired because of the structure of the housing of the protective goggles, resulting, as shown, in a substantial, if not total, loss of the field of vision through the lower segment 25 of bifocal lens 23.

FIG. 3 shows in conjunction with the protective goggles 10 of this invention a wearer's eye and a bifocal lens also represented at 22 and 23, respectively. From the broken vision lines represented in FIG. 3, it can be seen that the unique structure of tubular member or housing 11 provides a substantially full field of vision for the wearer through viewing aperture 15 including a substantially full field of vision through the lower segment 25 of corrective bifocal lens 23. The protective goggles of this invention, therefore, provides for a full, uninterrupted field of vision while continuing to provide maximum eye protection for the wearer with a minimum of wearing discomfort.

While I have described only a single preferred embodiment of my invention, persons skilled in this art will appreciate changes and modifications which may be made without departing from the spirit of my invention. Therefore, I do not intend to be limited except by the scope of the following appended claims.

I claim:

1. Protective goggles for welders, chippers, and the like, particularly adapted for wearers of corrective bifocal lenses which comprises: a generally tubular shaped protective member; an open end to said tubular member contoured to fit snugly against the face about the eyes of the wearer, said open end having an axis on approximately the same horizontal plane as the axes of the eyes of the wearer when looking straight ahead; a generally planar closed viewing end to said tubular member having at least one viewing aperture, a cylindrical lens holder mounted in said viewing end of said tubular member adjacent said viewing aperture, a replaceable safety lens mounted in said lens holder, said lens holder and said safety lens having a central axis, said central axis of said lens holder and said safety lens intersecting the axis of the open end of said tubular member at an angle from below it, the degree of the included angle formed by the intersecting axes being predetermined so that the closed viewing end is tilted in relation to the open end such that the wearer of the goggles when using corrective bifocal lenses underneath them will have an unobstructed view through the lower portion of the bifocal lens and through the safety lens.

2. The protective goggle according to claim 1 in which said lens holder is a cup type lens holder extending outwardly from the plane of the closed viewing end of said tubular member.

* * * * *